(12) United States Patent
Epstein

(10) Patent No.: US 12,116,558 B2
(45) Date of Patent: Oct. 15, 2024

(54) DEVICE FOR HIGH THROUGHPUT ISOLATION AND CULTIVATION OF MICROBIAL SPECIES

(71) Applicant: Northeastern University, Boston, MA (US)

(72) Inventor: Slava Epstein, Dedham, MA (US)

(73) Assignee: Northeastern University, Boston, MA (US)

( * ) Notice: Subject to any disclaimer, the term of this patent is extended or adjusted under 35 U.S.C. 154(b) by 566 days.

(21) Appl. No.: 17/228,528

(22) Filed: Apr. 12, 2021

(65) Prior Publication Data

US 2021/0317397 A1 Oct. 14, 2021

Related U.S. Application Data

(60) Provisional application No. 63/008,621, filed on Apr. 10, 2020.

(51) Int. Cl.
| | | |
|---|---|---|
| *C12M 3/00* | (2006.01) | |
| *C12M 1/00* | (2006.01) | |
| *C12M 1/04* | (2006.01) | |
| *C12M 1/12* | (2006.01) | |

(52) U.S. Cl.
CPC ............ *C12M 29/04* (2013.01); *C12M 23/14* (2013.01); *C12M 23/24* (2013.01); *C12M 37/02* (2013.01)

(58) Field of Classification Search
CPC ...... C12M 29/04; C12M 23/14; C12M 23/24; C12M 37/02; C12M 23/42; C12M 33/04; C12M 25/04; C12M 25/06; C12M 29/10; C12M 3/006; C12M 1/14; C12M 1/20; C12M 23/12
See application file for complete search history.

(56) References Cited

U.S. PATENT DOCUMENTS

| | | | | |
|---|---|---|---|---|
| 6,494,614 | B1* | 12/2002 | Bennett | B01F 33/304 |
| | | | | 422/615 |
| 7,011,957 | B2 | 3/2006 | Lewis et al. | |
| 9,249,382 | B2 | 2/2016 | Gavrish et al. | |
| 9,995,411 | B1* | 6/2018 | Moorman | F16K 99/0036 |
| 2006/0204445 | A1* | 9/2006 | Atala | A61K 47/6923 |
| | | | | 424/423 |
| 2007/0231887 | A1* | 10/2007 | McGrath | C12M 29/04 |
| | | | | 435/297.5 |
| 2007/0275451 | A1 | 11/2007 | Gavrish et al. | |

(Continued)

FOREIGN PATENT DOCUMENTS

WO    2016187622 A1    11/2016

OTHER PUBLICATIONS

Son, K.J. et al., "Microfluidic compartments with sensing microbeads for dynamic monitoring of cytokine and exosome release from single cells", Analyst, (2015), 10 pgs. (Accepted manuscript).

(Continued)

*Primary Examiner* — Nathan A Bowers
(74) *Attorney, Agent, or Firm* — Verrill Dana, LLP

(57) ABSTRACT

High capacity, low cost devices for use in growing monocultures of novel, previously unknown microbial species contain adhesive layers with wells covered by nanoporous membranes. The devices are placed in natural environments for cultivation of unknown microbial species.

13 Claims, 5 Drawing Sheets

(56) References Cited

U.S. PATENT DOCUMENTS

2012/0285560 A1\* 11/2012 Cooksey ............ B81C 1/00119
   137/561 A
2017/0145363 A1\* 5/2017 Hsu ........................ C12M 33/04
2018/0155664 A1\* 6/2018 Domenech ............ C12M 21/08
2018/0155759 A1 6/2018 Epstein

OTHER PUBLICATIONS

Chiu, Y-J et al., "A single-cell assay for time lapse studies of exosome secretion and cell behaviors", Small, Jul. 2016; 12(27) pp. 3658-3666 (Author manuscript).

Nichols, D. et al., "Use of Ichip for High-Throughput In Situ Cultivation of "Uncultivable" Microbial Species", Applied and Environmental Microbiology, Apr. 2010, vol. 76, No. 8, pp. 2445-2450.

Kaeberlein, T. et al., "Isolating "Uncultivable" Microorganisms in Pure Culture in a Simulated Natural Environment", Science, May 10, 2002, vol. 296, pp. 1127-1129.

\* cited by examiner

DEVICE FOR HIGH THROUGHPUT ISOLATION AND CULTIVATION OF MICROBIAL SPECIES

CROSS-REFERENCE TO RELATED APPLICATIONS

This application claims priority to U.S. Provisional Application No. 63/008,621, filed 10 Apr. 2020, which is incorporated by reference herein in its entirety.

STATEMENT REGARDING FEDERALLY SPONSORED RESEARCH OR DEVELOPMENT

This invention was made with government support under Grant Numbers HG005816 and DE020707 awarded by the National Institutes of Health, Grant Numbers 1203857 and 1650186 awarded by the National Science Foundation, and Grant Number W911NF-19-C-0008 awarded by DARPA. The government has certain rights in the invention.

BACKGROUND

Microbial discovery in the environment and in the human microbiome has uncovered only a small part of existing microbial diversity. The majority of environmental microbes and the microbiome remains undiscovered and includes unexplored species. Typical microbial cultivation techniques have failed to isolate and grow the majority of microbial species growing in diverse environments. Opportunities to discover new microbes in the biosphere would benefit from new techniques and devices for microbial cultivation capable of isolating and cultivating previously unexplored microbial species.

SUMMARY

The present invention provides high capacity, low cost devices for use in growing monocultures of novel, previously unknown species of bacteria or other microbial species in their natural environments. The devices can be mass produced using inexpensive materials and conveniently assembled and loaded with environmental cells targeted for implantation in natural environments for cultivation.

The present invention can be further summarized by the following list of features.

1. A device for cultivation of microbial cells in contact with an environment, the device comprising:
   an adhesive layer;
   a first removable protective layer in contact with a first side of the adhesive layer; and
   a second removable protective layer in contact with a second side of the adhesive layer;
   wherein the adhesive layer, the first protective layer, and the second protective layer form a planar composite structure; and
   wherein the composite structure comprises a plurality of holes penetrating through the adhesive layer, a longitudinal axis of the holes disposed substantially perpendicular to a plane of the composite structure.
2. The device of feature 1, wherein the plurality of holes penetrate through the first protective layer, the adhesive layer, and the second protective layer.
3. The device of feature 1 or feature 2, wherein the holes have a diameter in the range from about 100 microns to about 3000 microns.
4. The device of any of the preceding features, wherein the device comprises 96, 384, or 1536 holes.
5. The device of any of the preceding features, wherein the adhesive layer has a thickness of from about 50 microns to about 100 microns.
6. The device of any of the preceding features, wherein the adhesive layer has a melting point higher than about 121° C.
7. The device of any of the preceding features, wherein the adhesive layer comprises a silicone adhesive or a synthetic rubber adhesive.
8. The device of any of the preceding features which is sterile and packaged to maintain sterility until use.
9. A kit comprising the device of feature 1 and one or more nanoporous membranes.
10. The kit of feature 9, wherein the one or more nanoporous membranes comprise nanopores having a diameter in the range from about 10 nm to about 50 nm.
11. A device for cultivation of microbial cells in contact with an environment, the device comprising:
    a rigid support layer;
    a first adhesive layer in contact with a first side of the support layer and a second adhesive layer in contact with a second side of the support layer;
    a first removable protective layer in contact with the first adhesive layer on a side opposite the support layer and a second removable protective layer in contact with the second adhesive layer on a side opposite the support layer;
    wherein the support layer, the first adhesive layer, the second adhesive layer, the first removable protective layer, and the second removable protective layer form a planar composite structure; and
    wherein the composite structure comprises a plurality of holes penetrating through the composite structure, a longitudinal axis of the holes disposed substantially perpendicular to a plane of the composite structure.
12. The device of feature 11, wherein the plurality of holes penetrate through the first protective layer, the first adhesive layer, the support layer, the second adhesive layer, and the second protective layer.
13. The device of feature 11 or feature 12, wherein the holes have a diameter in the range from about 100 microns to about 3000 microns.
14. The device of any of features 11-13, wherein the device comprises 96, 384, or 1536 holes.
15. The device of any of features 11-14, wherein the first and second adhesive layers each have a thickness of from about 50 microns to about 100 microns.
16. The device of any of features 11-15, wherein the first and second adhesive layers each have a melting point higher than about 121° C.
17. The device of any of features 11-16, wherein the first and second adhesive layers each comprise a silicone adhesive or a synthetic rubber adhesive.
18. The device of any of features 11-17 which is sterile and packaged to maintain sterility until use.
19. A kit comprising the device of any of features 11-18 and one or more nanoporous membranes.
20. The kit of feature 19, wherein the one or more nanoporous membranes comprise nanopores having a diameter in the range from about 10 nm to about 50 nm.
21. A method of cultivating microbial cells in contact with an environment, the method comprising the steps of:

(a) providing the device of any of features 1-8 and a liquid suspension suspected of containing microbial cells obtained from an environmental sample;
(b) removing the first removable protective sheet from the device;
(c) replacing the first removable protective sheet with a first nanoporous membrane, wherein the first nanoporous membrane comprises a plurality of nanopores having diameters smaller than the microbial cells, and wherein the plurality of holes are sealed to form wells with the first nanoporous membrane forming bottoms of the wells;
(d) removing the second removable protective sheet;
(e) adding aliquots of the liquid suspension to the wells;
(f) placing a second nanoporous membrane on the adhesive where the second removable protective sheet had been, thereby sealing the wells, wherein the second nanoporous membrane comprises a plurality of nanopores having diameters smaller than the microbial cells; and
(g) placing the device into an environment suspected of supporting growth of the microbial cells, whereby a culture of microbial cells grows in one or more of the wells.

22. The method of feature 21, further comprising diluting the liquid suspension suspected of containing microbial cells so that a volume of the diluted suspension that fills a single well formed in step (c) contains about one microbial cell.

23. The method of feature 21 or feature 22, further comprising, after step (g), removing the device from the environment suspected of supporting growth of the suspected microbial cells, and collecting microbial cells from one or more wells of the device.

24. A method of cultivating microbial cells in contact with an environment, the method comprising the steps of:
(a) providing the device of any of features 11-18 and a liquid suspension suspected of containing microbial cells obtained from an environmental sample;
(b) removing the first removable protective sheet from the device;
(c) replacing the first removable protective sheet with a first nanoporous membrane, wherein the first nanoporous membrane comprises a plurality of nanopores having diameters smaller than the microbial cells, and wherein the plurality of holes are sealed to form wells with the first nanoporous membrane forming bottoms of the wells;
(d) removing the second removable protective sheet;
(e) adding aliquots of the liquid suspension to the wells;
(f) placing a second nanoporous membrane on the adhesive where the second removable protective sheet had been, thereby sealing the wells, wherein the second nanoporous membrane comprises a plurality of nanopores having diameters smaller than the microbial cells; and
(g) placing the device into an environment suspected of supporting growth of the microbial cells, whereby a culture of microbial cells grows in one or more of the wells.

25. The method of feature 24, further comprising diluting the liquid suspension suspected of containing microbial cells so that a volume of the diluted suspension that fills a single well formed in step (c) contains about one microbial cell.

26. The method of feature 24, further comprising, after step (g), removing the device from the environment suspected of supporting growth of the suspected microbial cells, and collecting microbial cells from one or more wells of the device.

As used herein, the term "about" refers to a range of within plus or minus 10%, 5%, 1%, or 0.5% of the stated value.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with the alternative expression "consisting of" or "consisting essentially of".

BRIEF DESCRIPTION OF THE DRAWINGS

FIG. 3A shows the device as presented to the user. FIG. 3B shows the device being dipped into and filled with a dilution of environmental microbes in molten agar. FIG. 3C shows the removal of a protective sheet from the adhesive layer on one side of the device. FIG. 3D shows a nanoporous membrane being bound to the exposed adhesive layer. FIG. 3E shows removal of the contents of a growth chamber after growth in an environment. FIG. 3F shows a manifold for high throughput recovery of growth chamber contents from a device using a microtiter plate format.

DETAILED DESCRIPTION

The present invention provides high capacity, low cost devices for use in growing monocultures of novel, previously unknown species of bacteria or other microbial species in their natural environments. The devices can be mass produced using inexpensive materials and conveniently assembled and loaded with environmental cells targeted for implantation in natural environments for cultivation.

Figure 1:
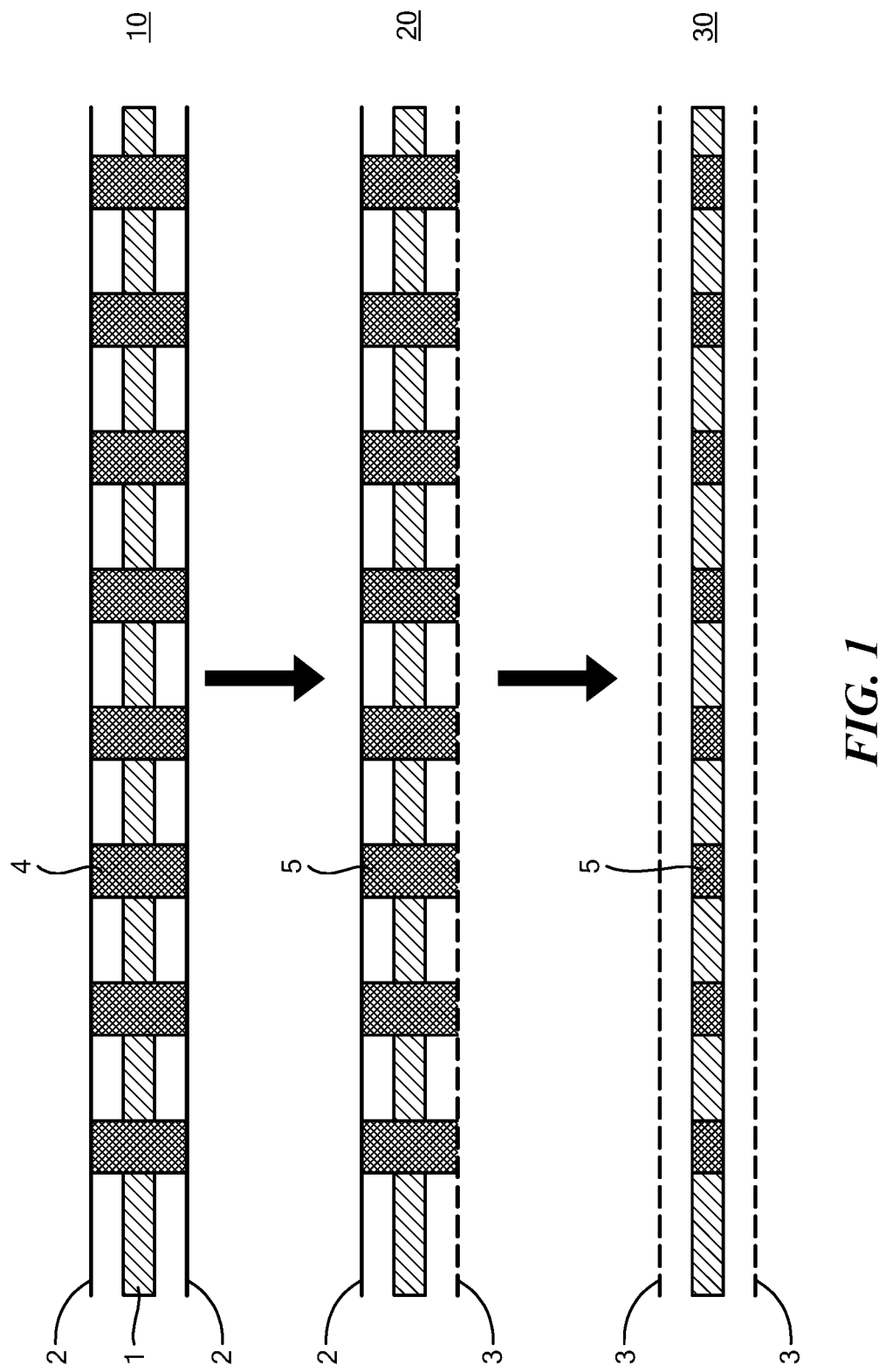
FIG. 1 depicts an embodiment of a device and process for high throughput screening of environmental microorganisms.

FIG. 1 depicts a first device 10 ("flexible embodiment") as provided to the user. The device 10 contains a center layer of adhesive 1 covered by outer layers 2 on both sides of the adhesive layer. The outer layers serve as protective layers for the adhesive and can be peeled away by the user. All three layers can be perforated by a plurality of holes 4, and each hole in the adhesive layer serves as an incubation chamber or well. In another configuration, the outer layers are not perforated by the holes. The holes can of any desired size, such as about 100 to about 3,000 microns in diameter. The diameter of the wells can be selected, for example, according to whether visual inspection of the wells is desired, and according to the desired magnification preferred for any inspection. The number of holes (wells) can be any number, but is preferably 96, or 384, or 1536, or any fraction thereof. For example, the number of wells can correspond to the format of standard microtiter plates, or a portion thereof (e.g., a fraction of the plate such as one-half, one-third, one fourth, or one-fifth of a plate, or a selected number of adjacent wells, rows, or columns of the plate), to which cultures can be transferred and used for subsequent subculturing, including by automated equipment.

The central adhesive layer 1 can be any suitable adhesive. Examples are silicone adhesive or synthetic rubber adhesive materials, such as 3M 1567. Such adhesives are commercially available as films with protective sheets covering both surfaces, making them well suited for use in the present invention. The protective sheets, or release sheets, are designed to protect the surfaces of the adhesive layer from adhering to undesired objects; the protective sheets can be made of thin paper or plastic such as, for example polyester or polyethylene terephthalate (PET). The adhesive layer is preferably non-toxic and non-inhibiting to the growth and culturing of microorganisms. The adhesive layer can be about 10 microns to about 300 microns in thickness, about 25 microns to about 200 microns in thickness, or about 50 microns to about 100 microns in thickness. The adhesive material, and preferably also the protective sheet material, can have a melting point above 121° C. to permit autoclaving for sterilization. Alternatively, for example, if the melting point is too low to permit autoclaving, the device can be sterilized using radiation, such as electron beam radiation or gamma radiation. Either before or after sterilization, device 10 can be sealed in an airtight package to be delivered to the user in sterile condition. A synthetic rubber can be a natural rubber including an additive. Suitable silicone adhesives may include, for example, siloxanes and silicones, di-methyl, hydroxy-terminated, dimethicone, silane, dichlorodimethyl-silane, or reaction products with silica, gamma-glycidoxypropyl-trim ethoxysilane, octamethylcyclotetrasiloxane, ethyltriacetoxy-silane, methylsilanetriol triacetate, curing agents, dibutyltin dilaurate, tin, and/or platinum. The adhesive should be capable of spontaneously forming a seal with the nanoporous membrane of the device that allows the nanoporous membrane to cover the wells in a leakproof manner, and yet allows the nanoporous membrane to be later peeled away for access to microbial cultures within the wells.

Following collection of cells from an environmental sample, such as soil, water, ice, rock, or extraterrestrial material, the cells can be loaded into the device, preferably in a laboratory under sterile conditions. Referring to FIG. 1, first one protective sheet 2 is removed from the adhesive and replaced with a nanoporous membrane 3, such as a polycarbonate membrane containing pores having a diameter from about 10 nm to about 50 nm in diameter, or such as about 20 nm in diameter, yielding device 20. The thickness of the nanoporous membrane can be from about 5 to about 20 microns, for example. This first-applied nanoporous membrane serves as a base of the wells in the adhesive layer and, once assembled and placed into an environment, the pores allow chemicals from the environment to enter the wells without allowing cells to enter or leave.

In an alternative configuration, one or both of the nanoporous membranes depicted on either side of the device depicted in FIG. 1 can be provided underneath the protective sheets, as presented to the user. In this configuration, a protective sheet can be removed, leaving behind the underlying nanoporous membrane, or removed with the underlying nanoporous membrane. If the nanoporous membrane is removed with the protective sheet, the protective sheet can then be peeled away from the nanoporous membrane, which is then re-applied to the adhesive layer 1.

After the first nanoporous membrane is bound to one side of the adhesive layer and forms the bottom of the wells, a suspension of environmental cells 5 is placed into each well, after diluting a natural source of bacteria or other microbes to a concentration (such as from about 0.33 cells/nl to about 0.33 cells/µl) expected to provide about one cell per well. Dilution can be performed by adding a liquid obtained from the natural environment from which the microbes were harvested (e.g., sea water, ground water), and addition of a gellable substance is highly preferred. For example, each well can have a total volume of from about 3 nl to about 3 µl and can be fully filled with the cell suspension. Once the wells have been filled, the second protective sheet 2 is removed from the adhesive layer and replaced with a second nanoporous sheet 3 that is bound to the adhesive to seal device 30 such that no further microorganisms can enter the wells, yet chemical factors from the environment can enter and leave through pores in both nanoporous sheets. The device 30 can then be implanted into a selected environment, preferably an environment similar or identical to the environment from which the cells in the device were originally obtained.

Addition of a gellable polymer to the diluted cell solution offers the possibility to form a gel in the growth chamber of each well of the device before placing it into an environment for growth. The polymer can be added at a concentration of, e.g., 1.5 to 2.0% wt/wt, so as to produce a gel that is neither so soft that it runs out of the growth chambers when the membrane is removed, nor so firm that it is difficult to remove from the growth chambers. The gel also should have a melting temperature that allows living cells to be added to the molten gel without harm and that allows the gel state to remain stable at the intended environmental temperature. The presence of a gel assists in holding in place the contents of each well during manipulation of the device, such as attaching or detaching the nanoporous membrane, without the loss of material from the growth chambers. The presence of a gel may also encourage attachment of microbes to polymer strands of the gel and the formation of a biofilm, which can stimulate growth. Suitable gel forming polymers include any such polymers used to culture microbial cells in the laboratory, including natural polymers such as alginate, agarose, agar, gelatin, and collagen, as well as synthetic polymers such as poloxamer and polyacrylamide. The polymer can optionally be functionalized with a chemical or biological moiety to enhance or inhibit cell attachment, or to modulate cell activity. The pH or salinity of the diluted cell solution can be controlled by adding a pH buffer and/or electrolytes to set initial conditions favorable to cells of interest. If desired, a laboratory culture medium can be used as the liquid phase instead of a naturally occurring liquid. Nutritional additives in the form of proteins, peptone, blood, serum, sulphur, phosphorus, traces of metal salts, vitamins, and/or metabolites can be added; however, it is preferred to rely on components from the natural environment and to avoid such additives.

Initially, the diluted cell solution contains a desired low number of harvested environmental cells, such as a single cell, on average, in the volume corresponding to a single well. Alternatively, it may be desired to have a small number of cells in the volume of a growth chamber, such as 2, 3, 4, 5, 6, 7, 8, 9, or 10 cells, to allow for co-culturing of different types of cells to study their interactions.

It should be noted that two factors can reduce or eliminate the potential for contamination of the growth chambers during incubation in the environment. First, the choice of a suitable adhesive makes it possible to attach the nanoporous membrane without the need for further adhesives or structures to form a tight seal, even after optionally removing and replacing the membrane. If further seal reliability is desired, a additional silicone adhesive can be applied to seal the membrane to the device. Second, the use of a gel within the growth chambers keeps the contents of each chamber in place during harvesting and prevents cross-contamination. It is desirable to perform two types of control experiment in order to confirm the absence of contamination. In one experiment, no microbes are added to the growth chambers, and the sealed device is submerged into a culture of known microbes, such as *E. coli*. If the known microbes are later found in the growth chambers, after removing and suitably washing the device, then a leak pathway is identified. In the inverse experiment, known microbes can be placed into individual growth chambers, the device placed into an environment lacking microbes, and then the growth chambers separately harvested. The appearance of the known microbes in chambers that they were not added to indicates that cross-contamination has occurred.

After a period of incubation, which may last for hours, days, weeks, months, or even years depending on the expected growth cycle of the microbes or the accessibility of the environment, the device 30 is retrieved, one nanoporous membrane is peeled off, and grown material is collected individually from each well for subculturing. Alternatively, both nanoporous membranes can be removed and the contents of all wells is removed into a matching microtiter plate, for example, by means of a replicator with multiple pins. Harvesting of the growth chamber contents can be by manual retrieval from chambers individually, or can be automated using a device such as a microplate replicator which has an array of stainless steel pins for transfer of cells to new containers, or using a microplate aspirator, which can be air-sealed and used to push gel plugs out of the growth chambers into a fresh microwell plate.

In a second configuration ("rigid embodiment" shown in FIG. 2), base layer 6 is a planar rigid material, such as a polymer material. The base layer is covered on both faces with adhesive layer 1, which can be the same type of silicone adhesive or synthetic rubber as described above for the configuration shown in FIG. 1. The first adhesive layer on a first face of the base, as well as the second adhesive layer on the second face of the base, each contain a plurality of pores 4 designed to serve as wells for incubation of microbial cells. The polymer material of the base layer can include or consist of, for example, polystyrene, polyethylene, polycarbonate, Teflon, Delrin, or polyimide. The inclusion of a plastic base provides additional rigidity in use, making the device more robust in harsh environments as well as during handling in the laboratory. The adhesive material and pore diameter dimensions can be the same as described above for FIG. 1. Device 40 can be sterilized as described above for FIG. 1. Before or after sterilization, the device can be sealed in an airtight package to be delivered to the user in sterile condition.

In the rigid embodiment, each adhesive layer 1 is covered with a protective sheet 2 on the side opposite the side attached to the base layer 6. In the lab, each protective layer can be removed, the wells filled with cell suspension 5, and the wells covered with nanoporous membrane 3 deposited onto the exposed surface of the adhesive layer. Once the wells have been filled, a second protective sheet 2 is removed from the adhesive layer and replaced with a second nanoporous sheet 3 that is bound to the adhesive to seal device 50 such that no further microorganisms can enter the wells. The device is then incubated in natural environment as described above.

Each adhesive layer of the rigid device can be about 10 microns to about 300 microns in thickness, about 25 microns to about 200 microns in thickness, or about 50 microns to about 100 microns in thickness. The thickness of the base layer can be selected to provide varying degrees of flexibility or rigidity. For example, the base layer thickness can be about 100 microns, about 200 microns, about 300 microns, about 500 microns, or about 1 mm, or from about 100 microns to about 1 mm. The base layer serves as a rigid support layer for the nanoporous membranes, and also serves as the substrate within which the wells are formed.

Figure 2:
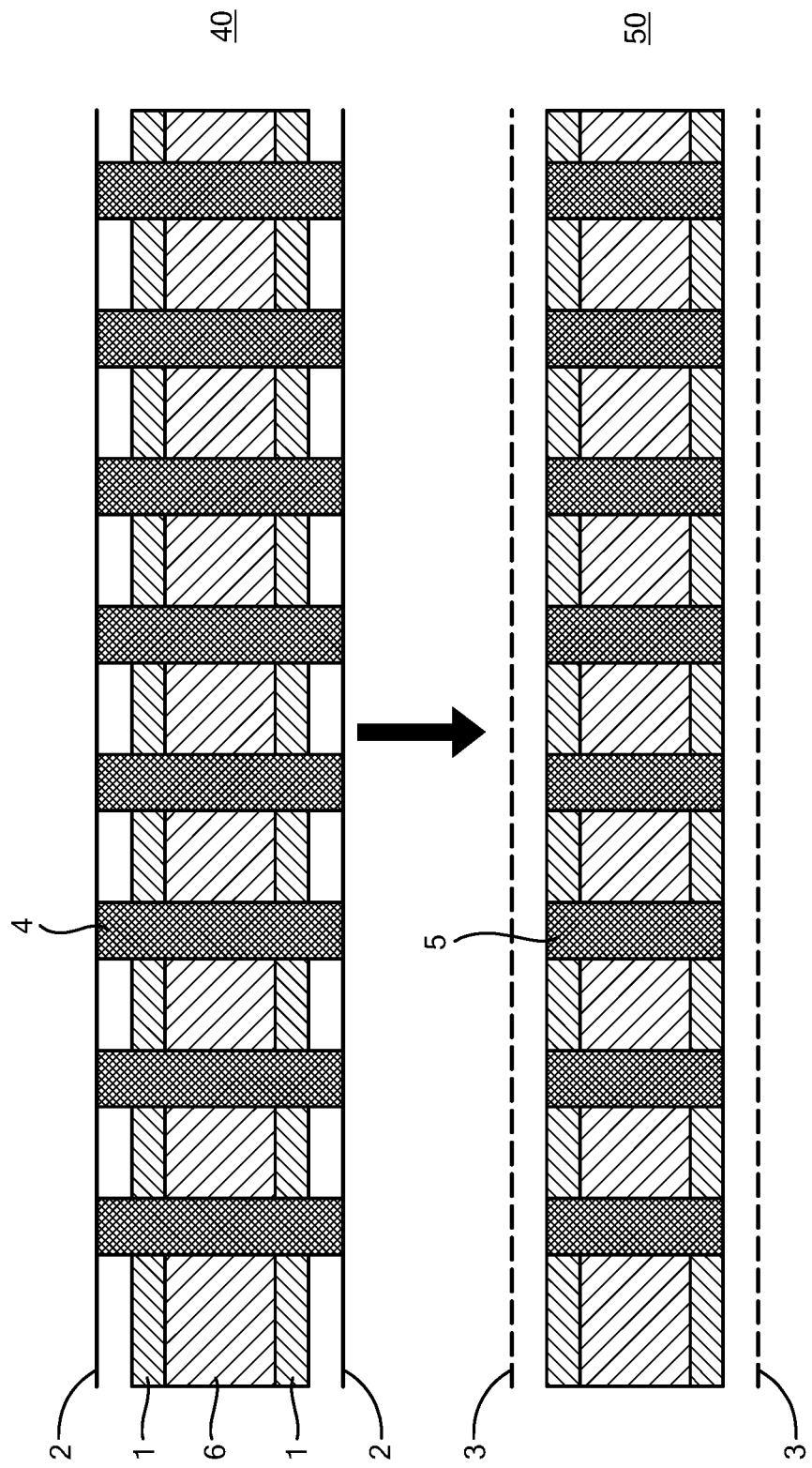
FIG. 2 depicts an embodiment of a device and process for high throughput screening of environmental microorganisms.
Figure 3B:
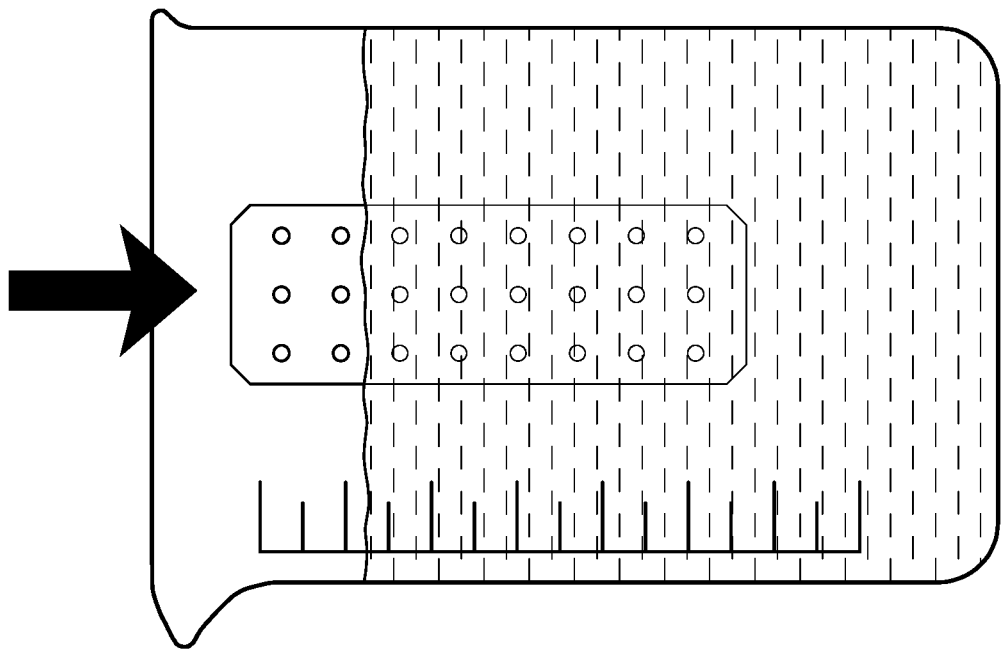
FIGS. 3A-3F depict an embodiment of a method of using a microbial culture device according to FIG. 2 for isolating monocultures of microorganisms from an environment.
Figure 3A:
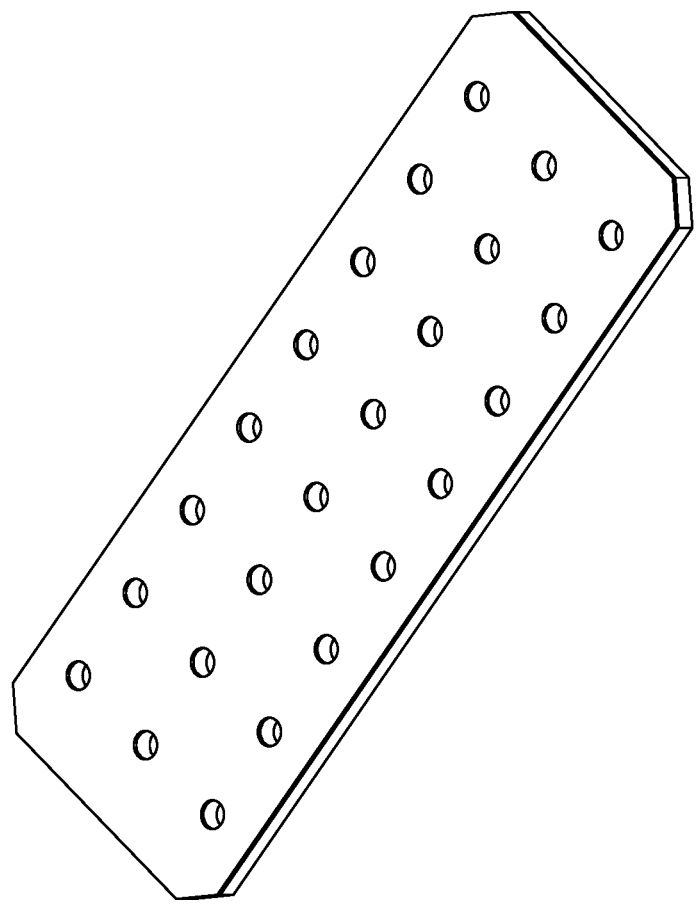
Figure 3C:
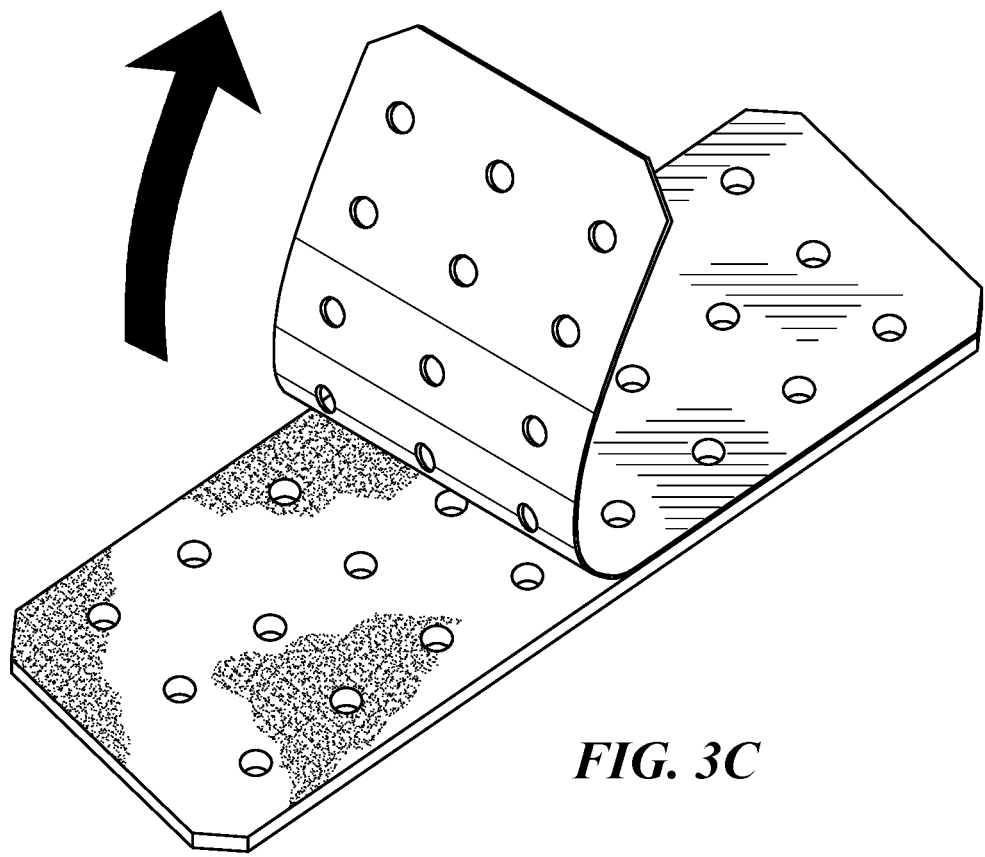
Figure 3D:
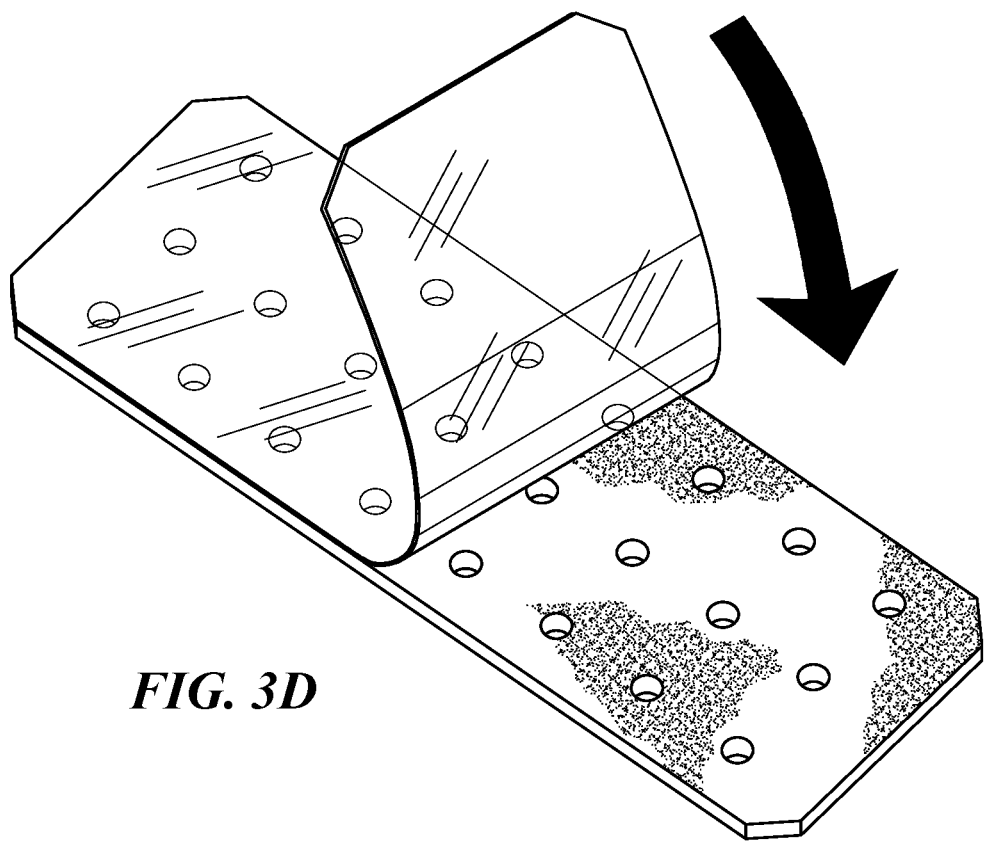
Figure 3E:
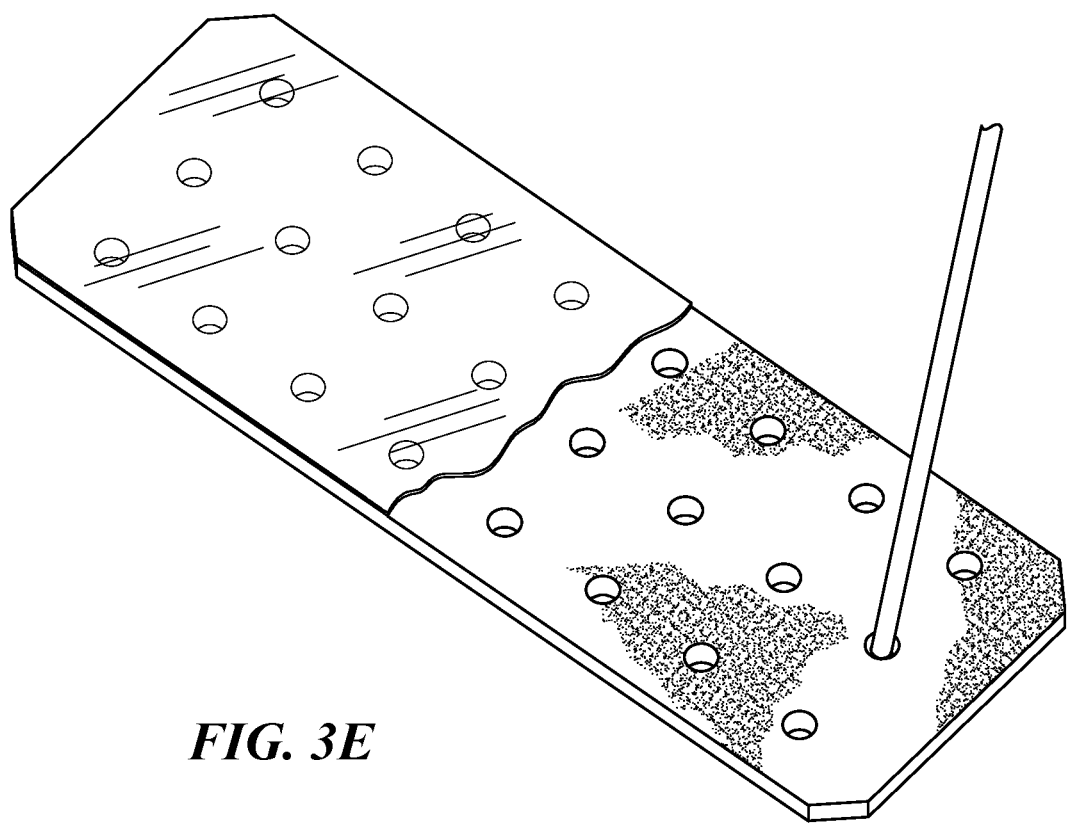
Figure 3F:
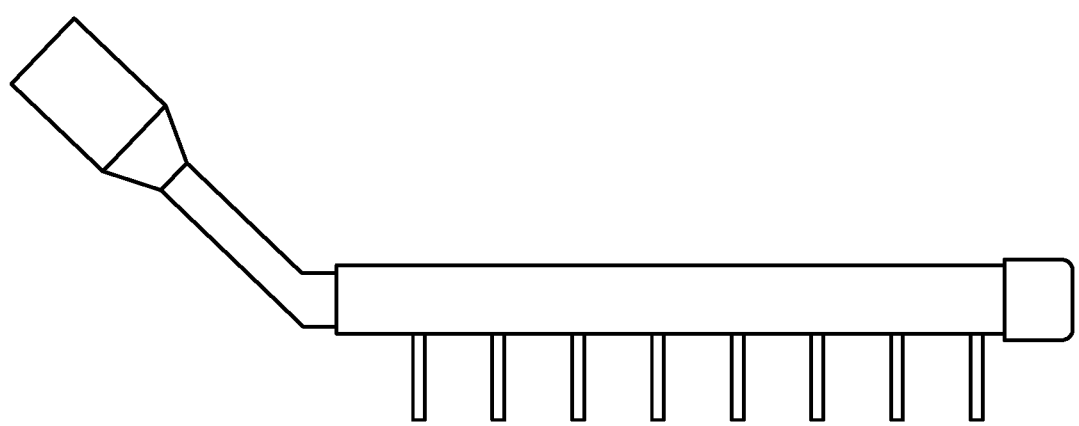

In an alternative configuration of the rigid embodiment, one or more of the nanoporous membranes depicted at either side of the device shown in FIG. 2 can be provided underneath the protective sheets. In this configuration, a protective sheet can be removed, leaving behind the underlying nanoporous membrane, or with the underlying nanoporous membrane. The protective sheet can then be peeled away from the nanoporous membrane, which is then re-applied to adhesive layer 1. A protective sheet can be removed, leaving behind a nanoporous membrane, depending upon the configuration.

After a period of incubation, the rigid device can be retrieved and processed in a similar manner as for the flexible embodiment. One membrane is peeled off, and the grown cells are collected from each well separately for subculturing and/or analysis. Alternatively, both membranes can be removed and the contents of all wells is removed into a matching microtiter plate, for example, by means of a replicator with multiple pins.

Holes in the adhesive layer or layers of a device can be prepared in a number of different ways. A preferred method is by drilling with a laser. For the rigid embodiment, the holes can be formed by injection molding of base 16 so as to produce a base layer containing the desired pattern of holes, which extend through the thickness of the base with openings on both sides. Yet another method of forming the holes is to use photolithography to form holes in either the adhesive layer and/or the base layer. In all embodiments, holes through different layers of the device must be aligned, i.e., the holes must exist in the base layer, if present, as well as in any adhesive layers and the protective layers. One way to achieve this is by first forming the layered structure without holes and then forming the holes through the entire structure; this is a convenient method for making the flexible embodiment. The devices of either embodiment can be fabricated using any known technique, including micromachining, laser drilling, photolithography, injection molding, three-dimensional printing, chemical etching lithography, any deposition method, or a combination thereof.

Few microorganisms from environmental samples grow on standard nutrient media in Petri dishes. However, once a device of the present invention is implanted into a selected environment, preferably an environment similar or identical to the environment from which the cells in the device were originally obtained, cells within the wells of the device are likely to grow because they are presented with their natural chemical milieu. The growth chamber of the device functions as a diffusion chamber within which previously uncultivatable microorganisms can be grown and later isolated. Rather than attempting to replicate the natural environment of a microorganism, the components of the environment can diffuse into the chamber. Simultaneously, the colonies in the chamber are confined within the chamber because the pores of the nanoporous membrane are smaller than the cells growing in the chamber. Addition of artificial growth media when diluting the cells to add to the device is optional.

The devices of the present invention can be provided in a kit. In addition to the microbial culture device, the kit can include, for example, additional nanoporous membranes, adhesive films, protective sheets, culture media or media components, one or more containers or reagents, and/or instructions for use. Such kits can be utilized for discovery of new microbial species.

A method to cultivate microbial species can include providing the device 10 of FIG. 1, and removing one protective sheet 2. An environmental sample suspected of containing a new microbial species is diluted to a concentration expected to have about one individual microbial cell in the volume of a single chamber of the device. The diluted cell suspension is then placed into chamber 4 under sterile conditions, and a nanoporous membrane 3 is applied to cover the wells and replace the protective sheet. The second protective sheet 2 is then removed from the opposite side of the device, and another nanoporous membrane 3 is applied to replace the second protective sheet, thereby sealing the growth chambers of the device, except for communication with the environment through the nanopores of the nanoporous sheets. The device is then placed into an environment similar or identical to the environment from which the microbes in the device were originally obtained, following which the device is incubated in the growth environment for a desired period of time (e.g., hours, days, weeks, months, or years) to allow growth of cultures within the growth chambers. If the original environmental sample was appropriately diluted, the result after the incubation period will be the occurrence of monocultures of microbial cells in at least some of the chambers. It may be desirable to place two or more devices into the same environment at the same time, or at different times. If two or more devices are used simultaneously, this can serve as a control for leakage or other failure in one of the devices. If two or more are used sequentially, information can be obtained about the changing microbial community and its evolution over time or in response to environmental change.

After the incubation period, the devices are retrieved. By placing the device into an environment similar or identical to the environment from which the microbes in the device were originally obtained, the microbes can receive naturally occurring nutrients or chemical modulators, which may be produced by other microbial cells in that environment. Some microbes grow best, or only, in an environment containing several different microbial species. The environment similar or identical to the environment from which the microbes in the device were originally obtained can, for example, include a gaseous environment, a wet environment, a solid environment (e.g., soil, rock, cement), a vacuum or partial vacuum environment (e.g., in outer space or on another planet, moon, or asteroid lacking an atmosphere), a pressured environment (e.g., undersea), or an extraterrestrial environment. Besides manual use, the methods and devices disclosed herein can be deployed by drones, probes, robots, or using other automated devices or techniques. The devices can include sensors, processors, memory, transmitters, and/or receivers for electromagnetic signals. For example, RFID tags can be included for easily locating a device within a location after an incubation period. A device is deployed to a far or isolated location and later retrieved with the help of such components.

The holes included in the devices can have any desired shape or profile. For example, they can be cylindrical, with or without parallel walls.

The devices can be fabricated using biocompatible, implantable materials, and then can be utilized for cultivation of microbes within a living organism to study or isolate components of the microbiome of the organism. In this example, a fluid or tissue sample suspected of containing microbes is taken from an organism. The fluid or tissue sample is processed (e.g., diluted, filtered, centrifuged, or disrupted to release microbial cells) and applied to one or more chambers of the device. The liquid is sealed into the device with one or more nanoporous membranes. Then, the device is implanted into the organism for cultivation. After an incubation period, the device is retrieved for analysis and/or further culturing.

EXAMPLES

Example 1. Cultivation of Bacteria from Marine Sediment

Bacterial cells are obtained from an intertidal sandy marine sediment. The cells are separated from sediment particles by vortex mixing, then serially diluted and mixed with warm agar made with seawater, and placed in a chamber of a device as shown in FIG. 1. The protective sheet is removed from one side of the device and replaced with a nanoporous sheet. The device is inverted, and the second protective sheet removed. The warm agar mixed with bacterial cells from the marine sediment sample is applied to completely fill all chambers of the device, and the top of the chamber is sealed with a second nanoporous membrane. The device is then placed back into the intertidal marine sediment from which the sample was taken. The device remains submerged in the sediment and in contact with moisture from tidal ocean water. The device is allowed to remain in place for one week, and is then recovered and brought to a laboratory. Colonies of bacteria are observed in some of the chambers and are observed and counted using an inverted fluorescence microscope at 1,000× magnification after staining with DAPI. The contents of the individual growth chambers are transferred to microtiter plates for high-throughput studies including PCR of the 16S ribosomal RNA gene to identify bacterial species.

The invention claimed is:

1. A device for cultivation of microbial cells in contact with an environment, the device comprising a composite structure consisting of:
   an adhesive layer consisting of an adhesive material and a plurality of holes penetrating through the adhesive material;
   a first removable protective layer in contact with a first side of the adhesive layer; and
   a second removable protective layer in contact with a second side of the adhesive layer;
   wherein a longitudinal axis of the holes is disposed substantially perpendicular to a plane of the composite structure, and wherein the holes penetrate through the first protective layer, the adhesive layer, and the second protective layer.

2. The device of claim 1, wherein the holes have a diameter in the range from about 100 microns to about 3000 microns.

3. The device of claim 1, wherein the device comprises 96, 384, or 1536 holes.

4. The device of claim 1, wherein the adhesive layer has a thickness of from about 50 microns to about 100 microns.

5. The device of claim 1, wherein the adhesive material has a melting point higher than about 121° C.

6. The device of claim 1, wherein the adhesive material is a silicone adhesive or a synthetic rubber adhesive.

7. The device of claim 1 which is sterile and packaged to maintain sterility until use.

8. A kit comprising the device of claim 1 and one or more separate sheets of nanoporous membranes.

9. The kit of claim 8, wherein the one or more separate sheets of nanoporous membranes comprise nanopores having a diameter in the range from about 10 nm to about 50 nm.

10. A method of cultivating microbial cells in contact with an environment, the method comprising the steps of:
 (a) providing the device of claim 1 and a liquid suspension suspected of containing microbial cells obtained from an environmental sample;
 (b) removing the first removable protective sheet from the device;
 (c) replacing the first removable protective sheet with a first nanoporous membrane, wherein the first nanoporous membrane comprises a plurality of nanopores having diameters smaller than the microbial cells, and wherein the plurality of holes are sealed to form wells with the first nanoporous membrane forming bottoms of the wells;
 (d) removing the second removable protective sheet;
 (e) adding aliquots of the liquid suspension to the wells;
 (f) placing a second nanoporous membrane on the adhesive where the second removable protective sheet had been, thereby sealing the wells, wherein the second nanoporous membrane comprises a plurality of nanopores having diameters smaller than the microbial cells; and
 (g) placing the device into an environment suspected of supporting growth of the microbial cells, whereby a culture of microbial cells grows in one or more of the wells.

11. The method of claim 10, further comprising diluting the liquid suspension suspected of containing microbial cells so that a volume of the diluted suspension that fills a single well formed in step (c) contains about one microbial cell.

12. The method of claim 10, further comprising, after step (g), removing the device from the environment suspected of supporting growth of the suspected microbial cells, and collecting microbial cells from one or more wells of the device.

13. The method of claim 10, wherein said environment is a natural environment selected from the group consisting of a gaseous environment, a wet environment, an undersea environment, a solid environment, a vacuum or partial vacuum environment, and an extraterrestrial environment.

* * * * *